(12) United States Patent
Jori

(10) Patent No.: US 6,454,951 B1
(45) Date of Patent: Sep. 24, 2002

(54) PHOTOSENSITIVE COMPOSITION

(75) Inventor: Guilio Jori, Padua (IT)

(73) Assignees: Giulio Jori, Padua (IT); Moshe Schaffer, Munich (DE); Alexander Holtz, Munich (DE)

(*) Notice: Subject to any disclaimer, the term of this patent is extended or adjusted under 35 U.S.C. 154(b) by 0 days.

(21) Appl. No.: 09/703,441

(22) Filed: Nov. 1, 2000

Related U.S. Application Data

(63) Continuation of application No. 09/125,442, filed as application No. PCT/EP97/00790 on Feb. 19, 1997, now abandoned.

(30) Foreign Application Priority Data

Feb. 19, 1996 (DE) .......................................... 196 06 081
Jun. 4, 1996 (DE) .......................................... 196 22 393

(51) Int. Cl.$^7$ ................................................ C02F 1/30
(52) U.S. Cl. .................... 210/748; 210/755; 210/763; 210/764; 210/501; 422/22; 428/403; 430/339; 514/454; 514/584; 514/587; 502/163; 502/167; 502/522
(58) Field of Search ........................ 210/748, 755, 210/763, 764, 501; 422/22, 24; 428/403; 430/339; 514/454, 584, 587; 502/5, 163, 167, 522

(56) References Cited

U.S. PATENT DOCUMENTS

| | | | | |
|---|---|---|---|---|
| 4,240,920 A | * | 12/1980 | de Luque | 252/99 |
| 4,315,998 A | | 2/1982 | Neckers et al. | 525/332 |
| 4,465,452 A | | 8/1984 | Masuzawa | 425/308 |
| 4,520,072 A | | 5/1985 | Yoshino et al. | 428/403 |
| 4,530,924 A | | 7/1985 | Polony et al. | 514/191 |
| 4,648,992 A | | 3/1987 | Graf et al. | 540/124 |
| 5,106,872 A | | 4/1992 | Alder et al. | 514/587 |
| 5,807,675 A | * | 9/1998 | Davalian et al. | 435/6 |
| 6,180,354 B1 | * | 1/2001 | Singh et al. | 435/7.1 |
| 6,251,581 B1 | * | 6/2001 | Vllman et al. | 435/4 |

FOREIGN PATENT DOCUMENTS

| WO | WO 90/06955 | 6/1990 |
|---|---|---|
| WO | WO 93/00815 | 1/1993 |

* cited by examiner

Primary Examiner—Peter A. Hruskoci
(74) Attorney, Agent, or Firm—Akin, Gump, Strauss, Hauer & Feld, L.L.P.

(57) ABSTRACT

The present invention relates to a composition comprising at least one photosensitizer of the tetrapyrrole and/or tetraazapyrrole series and a solid carrier which is swellable in water. Under the action of electromagnetic radiation the photosensitizer develops its antimicrobial action by way of the activation of oxygen and/or the promotion of processes in which free radicals are involved. Said composition is useful for treating water with the aim of freeing it of bacterial germs, algae, yeast and fungi.

6 Claims, 9 Drawing Sheets

PHOTOSENSITIVE COMPOSITION

CROSS REFERENCE TO RELATED APPLICATIONS

This is continuation of U.S. application Ser. No. 09/125,442, filed Dec. 16, 1998, now abandoned, which is a Section 371 National phase of International Patent Application No. PCT/EP97/00790, filed Feb. 19, 1997.

BACKGROUND OF THE INVENTION

The present invention relates to a composition comprising at least one photosensitizer and a solid carrier, wherein the photosensitizer is chemically bonded to said carrier and wherein said carrier is swellable in water, and to a process for combating bacterial germs, algae, yeast and fungi in water.

Over the years, water purity and its influence on the products in contact with the water has gained increasing importance. One of the greatest problems in providing clean water is bacterial contamination and contamination due to algae, yeast and fungi. There are numerous processes for preventing or removing such contamination from water, but all have certain disadvantages. Thus, for example the prior art includes processes in which chemicals, steam, UV light, sterile filtration or ozone are employed for disinfection. All these processes have disadvantages, however, which in some cases makes use on a large scale seem not very appropriate economically. Thus, for example, treatment with chemicals can adversely influence the quality of the water due to the chemicals introduced. Ultraviolet treatment involves the risk that disinfection is only partially carried out, especially in the case of relatively large amounts of water to be treated. Although sterile filtration is capable of eliminating bacterial germs to a certain degree, it is unsuitable for preventing renewed bacterial growth.

One field of use which necessitates sterilization of large quantities of water is fish farming, which in particular should also satisfy the increasing foodstuff requirements. The productivity of fish farms depends, inter alia, on the extent to which transmission of diseases to the fish being bred can be limited or prevented. Contamination of the water with germs, algae, yeast and fungi is particularly severe during seasons when the temperature is increased and bacterial growth and growth of algae, yeast and fungi thus rises. The stress conditions for the fish also increase because of reduced concentrations of dissolved oxygen, so that their susceptibility to disease increases.

In monocultures, such as fish farms, the large number of animals per unit volume of water increases the multiplication and spread of potentially pathogenic microorganisms which can infect the fish. The germ content of the water can thus adversely influence the productivity of the unit.

The terms "germs and/or microorganisms" relate to microbes especially microbes which can be pathogeous, as e.g. gram-positive, gram-negative bacteriae, algae, yeast and fungi, wherein said germs can be present alone or in combination with other microorganisms.

Numerous bacterial pathogens have been identified in water, including Gram-positive rod-shaped and coccal bacteria, aeromonads, myxobacteria, Gram-negative rod-shaped bacteria, vibrios and pseudomonads. In addition to the above-mentioned processes for sterilizing water, vaccines or the introduction of antimicrobial compounds have also been resorted to in particular as measures to suppress the spread of diseases. However, these measures are of limited efficacy and result in enormous costs, and furthermore represent a risk to the environment.

Ozone treatment of water is currently the most important process for sterilizing water. However, this process requires removal of the ozone from the treated water after conclusion of the ozone treatment, the removal of the ozone necessitating a high expenditure on apparatus.

Thus, for example, frequently used vaccines, especially inactivated bacterial cells or purified subcellular organelles, are often harmful to numerous constituents of sea water or fresh water systems, with the result that the ecological equilibrium system is disturbed. Similarly, antimicrobial substances, from antibiotics to various other chemicals, also have several disadvantages, such as, for example, the development of a resistant microflora and the transmission of resistance to other pathogens by means of plasmid transfer; release of active compounds into the water of the environment with possibly adverse effects on humans; deposition of degradation products of the chemicals introduced in the environment with possibly accumulating toxic effects on the organisms in the vicinity of the unit. Typical example of environmentally harmful chemicals which are used in the fish industry are chloramphenicol, chloramine B and T and tetracyclines.

U.S. Pat. No. 4,530,924 discloses a process for combating micro-organisms in or on organic or inorganic substrates. EP-A-0 054 992 describes bleach compositions containing a photo-activator. WO93/00005 refers to a method for inactivating pathogens in a body fluid. U.S. Pat. No. 4,648,992 and U.S. Pat. No. 4,465,452 describe water-soluble phthalocyanine compounds for bleaching textiles. WO93/00815 mentions compositions of a polymer and a photosensitizer having autosterile character on exposure to visible light.

BRIEF SUMMARY OF THE INVENTION

The present invention is accordingly based on the technical problem of providing a composition for combating bacterial germs, algae, yeast and fungi in water which has a high efficiency, preserves the environment and also can be carried out inexpensively on a large industrial scale.

This problem is solved according to the invention by a composition comprising at least one photosensitizer of the tetrapyrrole and/or tetraazapyrrole series and a solid carrier, characterized in that the photosensitizer is chemically bonded to said carrier and said carrier is swellable in water.

The present invention also relates to a process for combating bacterial germs, algae, yeast and fungi in water, wherein the germ-containing water is brought into contact with the composition according to the invention and is subjected to electromagnetic radiation.

Moreover, the present invention relates to the use of the above-mentioned composition for the treatment of water containing bacterial germs, algae, yeast and/or fungi.

BRIEF DESCRIPTION OF SEVERAL VIEWS OF THE DRAWINGS

FIG. 1 shows the effect of irradiation with visible light on the survival of *V. anguillarum* cells after incubation for 5 minutes with 10 μg/ml of tetra(4-N-methyl-pyridyl)porphine $T_4MPyP$ and various washing operations; ■0 washing operation, ●1 washing operation, ▼3 washing operations.

FIG. 2 shows the effect of irradiation with visible light on the survival of E. coli cells after incubation for 5 minutes with 10 μg/ml of T$_4$MPyP and various washing operations; ■0 washing operation, ●1 washing operation, ▼3 washing operations.

FIG. 3 shows the effect of irradiation with visible light on the survival of V. anguillarum cells after incubation for 5 minutes with di(4NMPy)Ph$_2$P (8.4 μM) in aqueous suspension, □0 washing operation, ○1 washing operation, Δ3 washing operations.

FIG. 4 shows the effect of irradiation with visible light on the survival of E. coli cells after incubation for 5 minutes with di(4NMPy)Ph$_2$P (8.4 μM) in aqueous suspension, □0 washing operation, ○1 washing operation, Δ3 washing operations.

FIG. 5 shows the effect of HP concentration in the incubation medium on the amount of porphyrin bound by cells of M. hominis (●,○), A. laidlawii+S(■,□) and A. laidlawii−S (▼,Δ) in the exponential (filled symbols) and stationary (open symbols) phases of growth. The incubation was performed at room temperature for 30 min and the cell-bound HP was estimated by a spectrophotofluorimetric procedure.

FIGS. 6 and 7 show the survival curves of C. albicans cells, obtained from brain heart broth, irradiated at different temperatures in the presence of 1 μg HP ml$^{-1}$ and plated on Sabouraud agar (FIG. 6) and brain heart agar (FIG. 7). Vertical bars indicate standard error.

FIG. 8 shows the survival of mycoplasma cells in the exponential (filled symbols) and stationary (open symbols) phases of growth after incubation with HP for 90 min in the dark. The initial cell concentrations [log(c.f.u.ml$^{-1}$] were 7 for M. hominis and 6 for A. laidlawii (+S and −S). Each point represents the mean of three independent experiments performed in duplicate. The largest standard error obtained [log(c.f.u.ml$^{-1}$] was 0.18; ●, ○, M. hominis; ■, □, A. laidlawii+S, ▼, Δ A. laidlawii−S.

FIG. 9 shows the time-dependence of cell survival upon visible light irradiation at 37° C. of M. hominis (●), A. laidlawii+S (■), A. laidlawii−S (▼) in the exponential phase of growth, in the presence of 0.1 μg HP ml$^{-1}$ the cells (initial concentrations as for FIG. 8) had been previously incubated with HP for 60 min in the dark at room temperature. Each point represents the mean of four independent experiments performed in duplicate. The largest standard error obtained [log(c.f.u.ml$^{-1}$] was 0.2.

FIG. 10 shows the survival curves of C. albicans cells, obtained from brain heart broth, exposed to visible light at 37° C. in the presence of 0.1 (○), 1 (□) and 10 (Δ) μg HP ml$^{-1}$ and plated on brain heart agar. Vertical bars indicate standard error.

FIG. 11 shows photoinhibition of the marine alga Phaeodactylum tricomutum (diatomea) using as photosensitizer the dicationic porphyrin, meso-diphenyl-di(N-methyl-pyridyl)porphine (abbreviated as Di(4NMPy)Ph$_2$P) with a porphyrin concentration of 8.4 μM; medium: aqueous solution at pH 7.4 containing 2.4×10$^5$ algae/ml; temperature: 16–18° C. (before and during irradiation); light source: full spectrum visible light (filament lamps), 10 mW/cm$^2$; protocol: after irradiation, the system was kept in the dark and incubated at 18° C.; viability counts were carried out at selected post-irradiation times; control: algae kept in the dark at 18° C.; light only: algae specimens irradiated in the absence of photosensitizer for 30 min.

The meanings of the symbols are:
OD$_{650}$: optical density at 650 nm (absorption)
—□—control
—○—+30 min light
—Δ—+porphyrin-light
—▲—+porphyrin+min light
—◇—+porphyrin+15 min light
—+—+porphyrin+30min light FIG. 12 shows an experiment which was carried out with a freshwater alga, namely a Clamydomonas sp., in the same manner used for the algae from a marine water as described above.

The evaluation of the legal growth at about 430 h after the end of the irradiation studies (post irradiation incubation) is shown:
—□—control (untreated algae):
—○—+Irradiated 30 min. in the absence of porphyrin:
—Δ—+Incubated with porphyrin in the dark:
—▲—+Irradiated with porphyrin for 1 min.:
—◇—Irradiated with porphyrin for 15 min.:
—+—+Irradiated with porphyrin for 30 min.:

The numbers are proportional to the number of algae per volume unit (ml).

Figure 13:
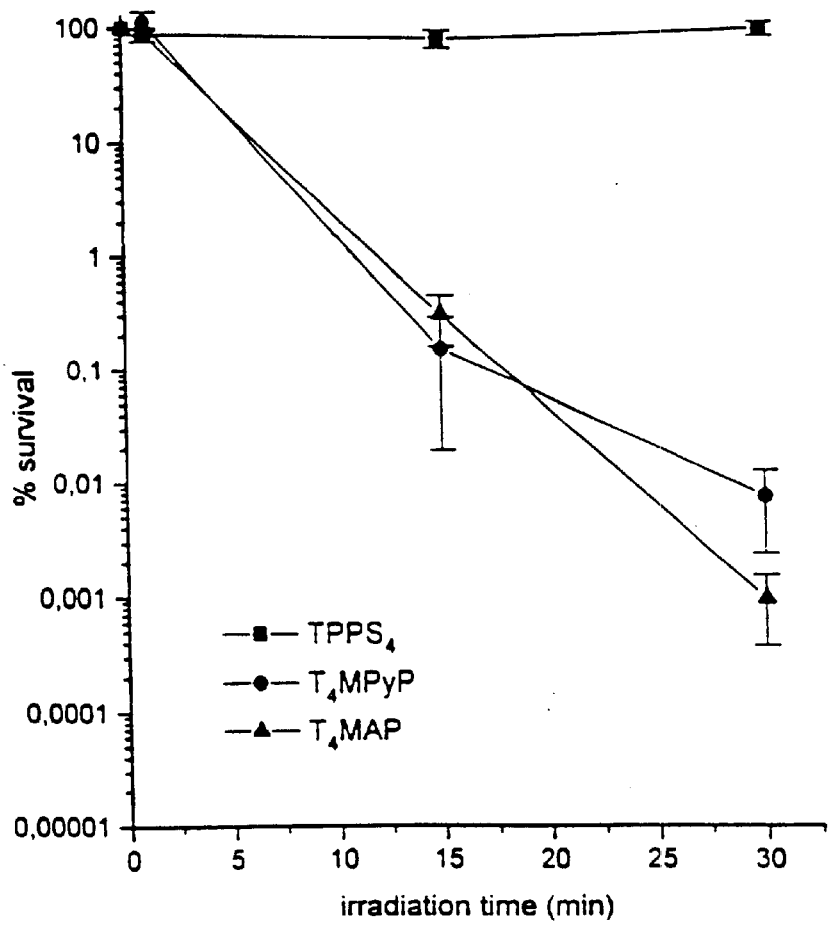

FIG. 13 shows the effect of visible light irradiation on cell survival of E. coli after 5 min incubation with 10 μg/ml of different porphyrins and without washing; ■ tetraphenylporphine sulfonate (TPPS$_4$), ● tetra(4-N-methyl-pyridyl) porphine (T$_4$MPyP), ▼ tetra(N,N,N-trimethyl-anilinium) porphine (T$_4$MAP).

Figure 14:
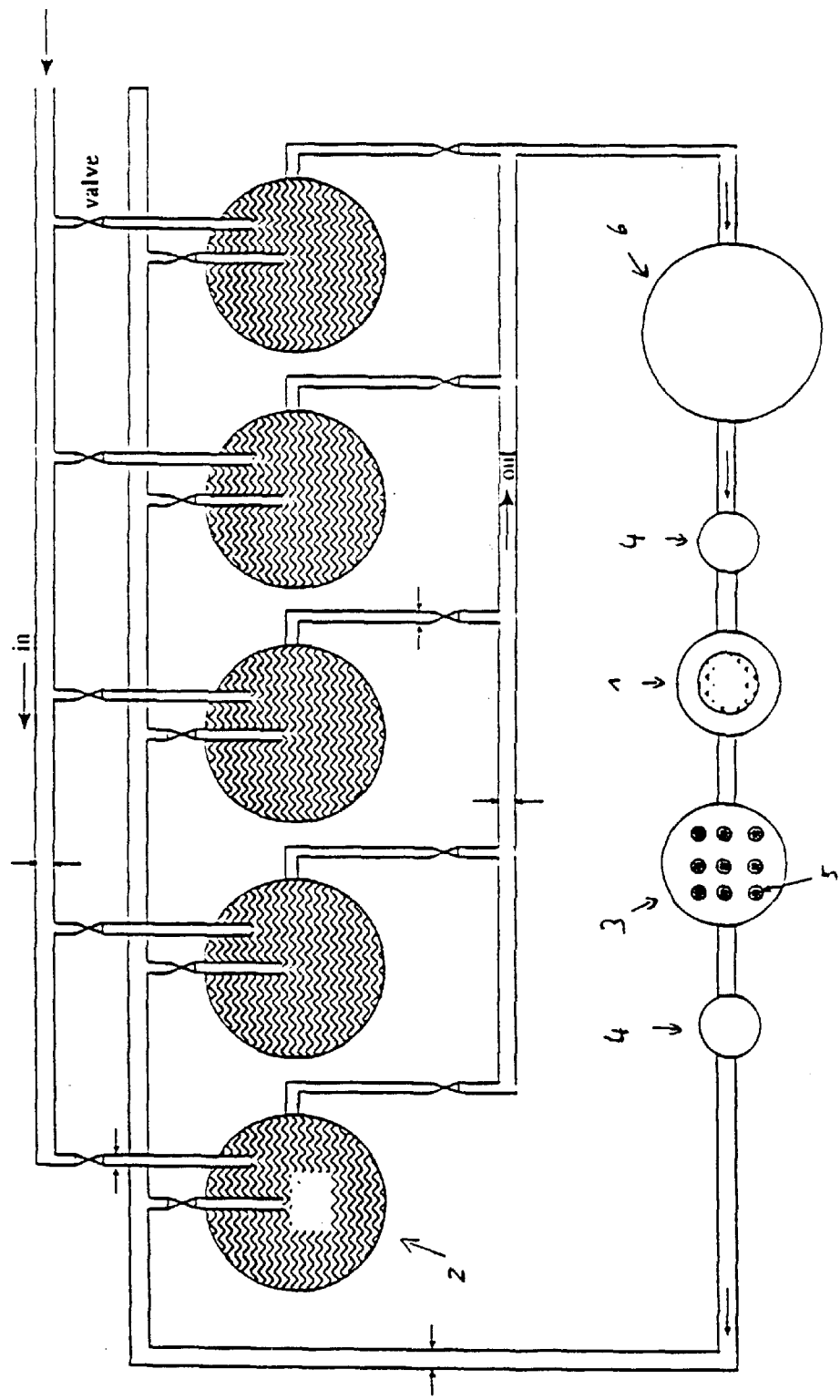
FIG. 14 shows a unit for treating water of a fish farm.

FIG. 14 shows a construction, given by way of example, of a unit for treatment of water using the process according to the invention, which unit can be modified in any desired manner by the different use of technical components according to the prior art available and the aim of its use.

DETAILED DESCRIPTION OF THE INVENTION

Gram-positive and also Gram-negative bacteria can be combated effectively by the composition according to the invention. In particular, however, the composition according to the invention has the advantage over alternative processes and compositions that even Gram-negative bacteria, which are resistant to numerous other chemicals, can be combated extremely effectively. Moreover, the composition of the present invention is effective against various algae, yeast and fungi as well.

It has surprisingly been found that photoinhibition of alga growth is caused by light exposure times of 15 min or longer, indicating that the irradiation systems appear to be very efficient in inducing the decrease in alga survival. It is evident that the porphyrin photosensitization has a very strong inhibitory effect on the growth of algae, the photoprocess appears to be even more efficient as compared with that described for algae from marine waters. Thus, porphyrins are very efficient and powerful agents for controlling the growth of various microorganisms and algae in water environments.

"Photosensitizers" here are to be understood as compounds which absorb electromagnetic radiation preferably visible light, and are able to catalyse the formation of free radicals and/or singlet oxygen from triplet oxygen under the influence of the radiation. Tetrapyrrole and/or tetraazapyrrole compounds which may contain at least one positive charge (cationic photosensitizers) can be also suitable for use in the present invention. A preferred group which can carry the positive charge in the molecule is a quaternary ammonium group. The nature of the substituents on the macrocyclic ring is of minor importance for the photochemical properties of the photosensitizers; they essentially influence the solubility properties. By controlled introduction of substituents, the expert can accordingly impart to the photosensitizer the desired solubility properties, while retaining the photochemical properties of the starting compounds. The expert has available a large number of commercially obtainable compounds which are suitable for the present purpose.

When a photosensitizer of this above-mentioned type is irradiated, preferably with light, it displays its antibacterial action via activation of oxygen and/or the promotion of processes in which free radicals participate. Radiation having a spectrum in the range of about 350–900 nm is preferably employed.

Typical examples of Gram-negative bacteria which are inactivated rapidly and efficiently by irradiation with visible light include *Escherichia coli, Pseudomonas aeruginosa* and *Vibrio anguillarum*, wherein photosensitizers containing at least one positive charge are preferred.

On the other hand, Gram-positive bacteria, such as staphylococci and streptococci, can also be inactivated with the composition according to the invention.

A positive charge, if necessary for the antibacterial activity, can be introduced into the molecule by any desired substituents of the macrocyclic radical at least one side chain particularly preferably containing at least one amino group or a mono-, di- and/or trialkyl derivative thereof. The positive charge can also, for example, be introduced into the molecule by an N-alkylpyridyl function. The number of positively charged substituents is preferably in the range from 1 to 4 The positive charge of the substituents can be neutralized by anions, for example halide ions, or by tosylate.

It is known that the metabolism of algae, especially blue-green algae, can be modulated through the use of light, including both the UV and the visible component of the solar spectrum.

However, it was surprisingly found that the photosensitivity of algae can be utilized also in a negative sense, namely for controlling or limiting their proliferation, which is a frequent effect occurring in waste-water. This can be successfully applied in the case of those filamentous or colonial forms, which can be hardly treated by chemical or biological procedures, due both to their intrinsic resistance to the action of exogenous agents and the possible dire consequence of such treatments for the environment.

Families of algae which are especially susceptible to porphyrin photosensitization with visible light (at overall light doses as low as 50 J/cm², with fluence rates in the order of 20–50 mW/cm², and photosensitizer doses as low as 1–10 μg/ml) include the Nostocaceae (e.g. Anabaena), the Rivulariaceae (e.g. Calotrix), the Oscillatoriaceae (e.g., Trichodesmium), marine algae (e.g. Phaeodactylum tricornutum) and freshwater alga (e.g. Clamydomonas) and examples of yeast and fungi which can be inactivated as well include *C. albicans, M. homini* and *A. laidlawii* (+S and −S).

Particularly preferred photosensitizers are compounds from the group consisting of bacteriochlorins, chlorins, porphycenes, porphyrins, phthalocyanines and naphthalocyanines. Porphycenes are tetrapyrrole derivatives, such as are described, for example, in E. Vogel, M. Köcher, H. Schmickler, J. Lex, (1986), Angewandte Chemie 98, page 262. They are electronic isomers of porphyrins, since they are characterized by an 18π electron cloud which is responsible for their aromatic properties, their absorption in the near UV/visible light and their fluorescence emission spectrum. Porphyrins likewise constitute an 18π electron system, but differ from the porphycenes in their chemical structure (in particular the number of carbon atoms or methine bridges which join the individual pyrrole rings: 1,1,1,1 in porphyrins; 2,0,2,0 in porphycenes). The properties of the absorption spectra, furthermore, are different, in particular the intensity and position of the Soret band in the near UV and the blue region (cf., for example, J. Walluc, M. Müller, P. Swiderek, M. Köcher, E. Vogel, G. Hohineicher, J. Michl, (1991), J. Amer. Chem. Society, 113: 5551). The photophysical oxygen-photoactivating properties of porphycenes have been investigated in detail (P. E. Anamenidia, R. W. Redmond, S. Nonell, W. Schuster, S. E. Braslawsky, K. Schaffner, E. Vogel, (1986) Photochem., Photobiol., 44: 555; and R. W. Redmond, S. Valduga, S. Nonell, S. E. Braslawsky, K. Schaffner, (1989), J. Photochem, Photobiol. 3: page 193, (1989). Porphycenes are efficient generators of singlet oxygen; they are therefore suitable for promoting inactivation of biological systems when activated by near UV or visible light.

The porphycenes preferably have the following common features:

a) they have four substituents in positions 2, 7, 12 and 17 of the tetrapyrrole macrocyclic radical; such substituents are usually four alkyl chains (for example tetrapropyl derivatives) or four alkoxy chains (for example tetramethoxy or tetraethoxy derivatives);

b) one side chain is in the 9-position, i.e. on a carbon atom lying between the rings. This substituent can be, for example, a hydroxyl derivative, an ester, an amide or an ether having an alkyl group of varying complexity; for example, the hydrocarbon chain contains 1 to 18 C atoms.

The substituents influence the physicochemical properties of the porphycenes, such as their solubility in organic solvents. However, the nature of these substituents has only a slight influence on the absorption and fluorescence emission spectra, and on the photochemical properties. Their influence on the generation of singlett oxygen and their antibacterial action are thus of only minor importance.

The basic framework of porphycenes is as follows:

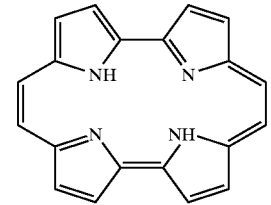

The introduction of a positive charge through a side chain in the above basic framework, if necessary, is familiar to the expert.

In addition to the porphycenes, members of the bacteriochlorins, chlorins, porphyrins, phthalocyanines and naphthalocyanines are also suitable compounds. The group of bacteriochlorins, chlorins, porphyrins, phthalocyanines and naphthalocyanines has been known for a long time and is described in detail in the literature. A large number of compounds are commercially obtainable. The introduction of the substituents or substituents carrying the positive charge into the molecule is also familiar to the expert.

The basic framework of porphyrins, bacteriochlorins, chlorins, phthalocyanines and napthalocyanines is as follows:

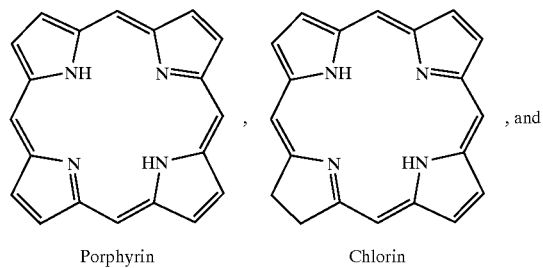

Porphyrin          Chlorin, and

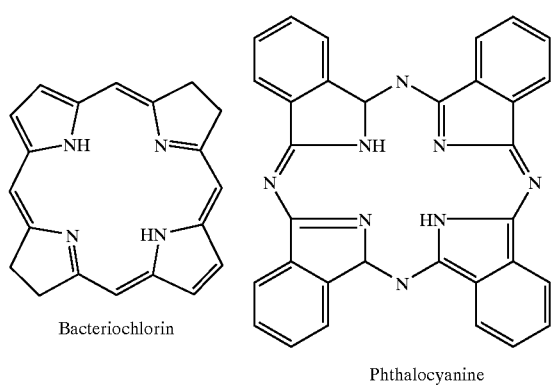

Bacteriochlorin          Phthalocyanine

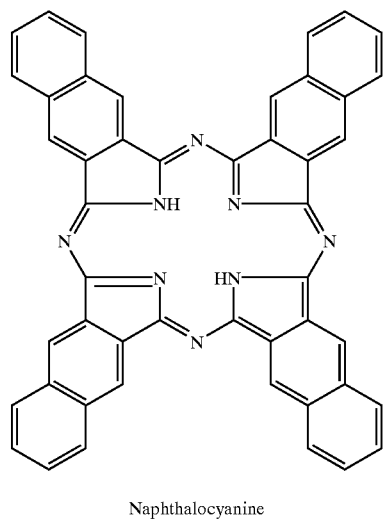

Naphthalocyanine

The photosensitizers can display particularly good antibacterial actions, especially against gram-negative bacteria, if they contain at least two positive charges in the molecule, and it is particularly advantageous if the two positive charges are in the meso-positions, so that there is an asymmetric distribution of the positive charges in the molecule. However, a molecule with a singlet positive charge already shows an antibacterial activity.

Bacteriochlorins, chlorins, porphyrins, phthalocyanines and napthalocyanines can bond a large number of different metal ions in the centre of the macrocyclic radical, wherein it is possible that in each case only one ion is bonded at the same time; the metal ion is bonded to the four nitrogen atoms of the pyrrole rings via coordinate bonds, wherein hybrid electron orbitals can participate in the bonding. Stable complexes can thus be prepared if metal ions which can form tetracoordinated or hexacoordinated complexes are used, pentacoordination also being permitted, and in some cases may even be preferred. Suitable metal ions comprise Zn, Al and Ge.

On the other hand, porphycenes are more difficult to convert into metal complexes, since the geometry of the macrocyclic radical is somewhat disturbed compared with porphyrins.

In a particularly preferred embodiment, several different photosensitizers are employed simultaneously. It is of advantage in particular here if the various photosensitizers are chosen such that the entire spectrum of visible light from 350 nm to 900 nm is utilized for the photosensitization. Compounds which have different absorption maxima are thus chosen, for example a compound having an absorption maximum at about 400 nm, a compound having an absorption maximum at about 500 nm and another compound having an absorption maximum at about 600 nm. Such a combination of photosensitizers with different absorption maxima has the advantage that daylight can be utilized particularly efficiently, especially taking into account the fact that the spectrum of daylight in the early hours of the morning and late hours of the evening differs from that of light at midday. In the case of applications where daylight is not available, the light can also be provided by means of conventional light sources, like tungsten filament lamps, halogen lamps, electroluminescence lamps and high pressure metal vapor lamps (e.g. sodium or mercury).

It is furthermore preferable if the photosensitizers employed are present in a form bonded to a solid carrier and are thus introduced into the water to be treated as part of a solid matrix. A polymer which carries the photosensitizer on it in a covalently bonded manner is particularly preferred as the carrier. It is preferred that the photosensitizer is covalently linked or anyhow associated in a very stable form (e.g. hydrophobically absorbed) with an inert support. The support can be represented by:

a finely dispersed colloidal particle or inorganic beads (e.g. clay); or a porous resin (e.g. Sephadex, Sepharose, Amberlite) which can be swollen by water.

The photosensitizer can be directly bound to the particle or the resin, otherwise a spacer made by an inert organic compound (e.g., a hydrocarbon chain, a polylysine chain, a polyethylenglycol chain, a polysaccharide chain) can be inserted between the resin/particle and the photosensitizer. These arrangements are purposely chosen in order to allow an intimate contact between the microbial cells which are present in the aqueous milieu and the photosensitizer, thereby ensuring maximal efficiency of the photosterilization process. A combination, comprising the carrier and the photosensitizer, develops the antibacterial activity as soon as it is exposed to light. Visible light in the range from about 350 to 900 nm is particularly preferred here.

The composition according to the invention can be employed in numerous fields of industry as a simple and extremely efficient water treatment process. The fields of use include, for example, waste water treatment, treatment of water for the drinks and foodstuffs industry, the pharmaceuticals, chemicals and cosmetics industry and the electrical industry, and furthermore treatment of drinking water, rainwater and also marine water, and, finally, the process according to the invention can also be used for treatment of water for use in air conditioning.

Said composition provides a high degree of safety and has been recognized as being environmentally friendly, since they utilize the combination of two agents (visible light and porphyrin-type photosensitizers) which are individually innoxious to the components of the ecosystem.

The following examples illustrate the invention.

Examples of compounds which, after introduction of at least one positive charge into the ring system, are suitable for the purposes of the present invention are given below.

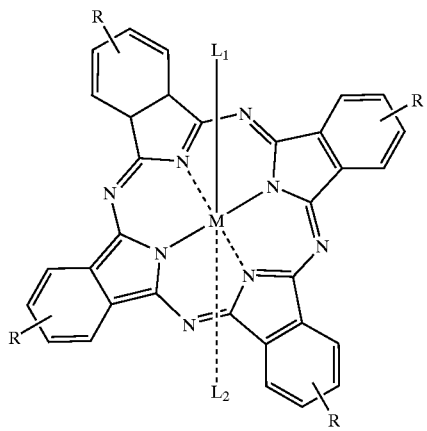

M=metal ion, e.g. Zn, Al, Ge

R=peripheral substituent for introduction of the positive charge $L_1$, $L_2$=axial ligand, e.g. siloxy-trialkyl ligand having the formula —OSi $R^1R^2R^3$, wherein $R^1$, $R^2$ and $R^3$ are independently selected from $CH_3$, $C_2H_5$, n-$C_6H_{13}$, n-$C_{10}H_{21}$ and —$(CH_2)_3O(CO)CH_3$

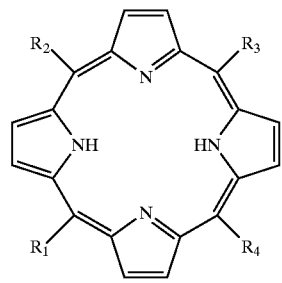

Meso-tetra(4-N-methyl-pyridyl)porphine:

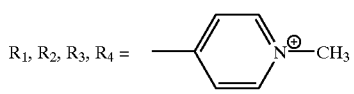

Meso-tetra(3-N-methyl-pyridyl)porphine:

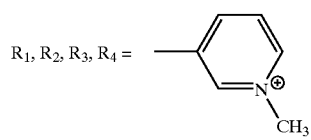

Meso-tri(4-N-methyl-pyridyl)monophenylporphine:

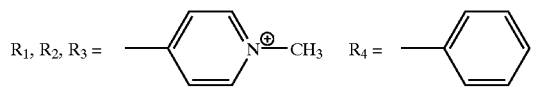

Meso-di(N-methyl-4-pyridyl)diphenylporphine:

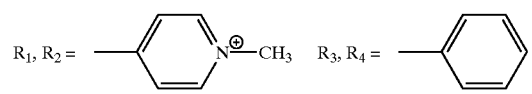

Meso-mono(N-methyl4-pyridyl)triphenylporphine:

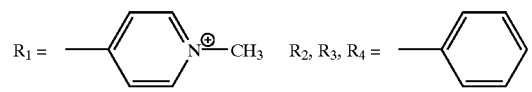

9-Hexyloxy-2,7,12,17-tetrakis(methoxyethyl) porphycene:

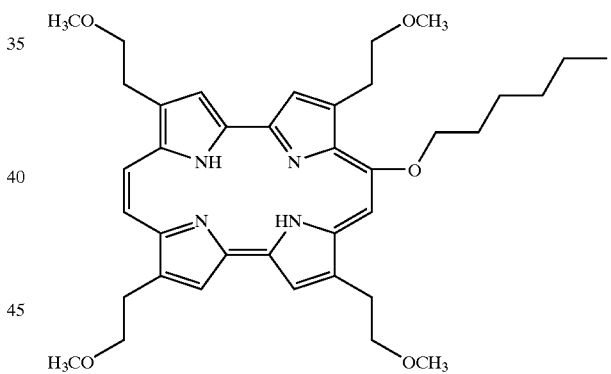

9-Methoxy-2,7,12,17-tetrakis(methoxyethyl)porphycene:

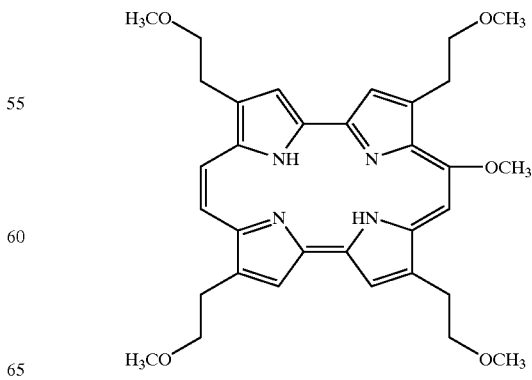

9-(Stearoylamide)-2,7,12,17-tetra(methoxyethel) porphycene:
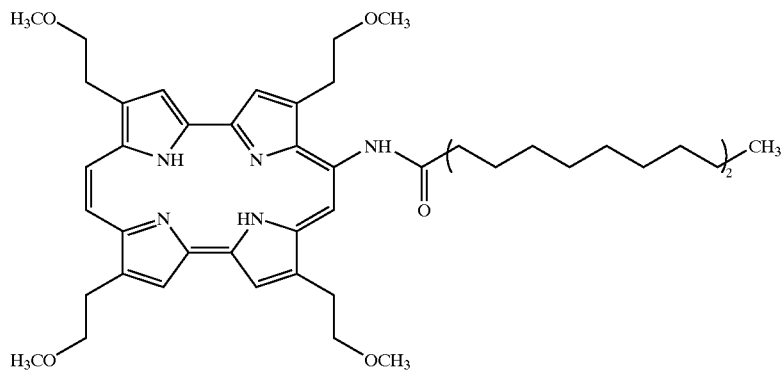
9-(Nikotinic acid amide)-2,7,12,17-tetrakis (methoxyethyl)porphycene:
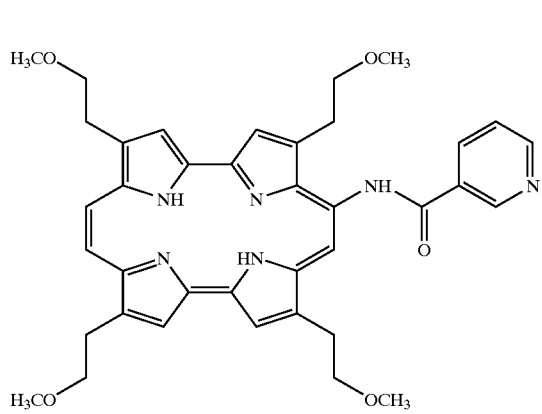
5,10,15,20-Tetrakis(m-hydroxyphenyl)bacteriochlorin:
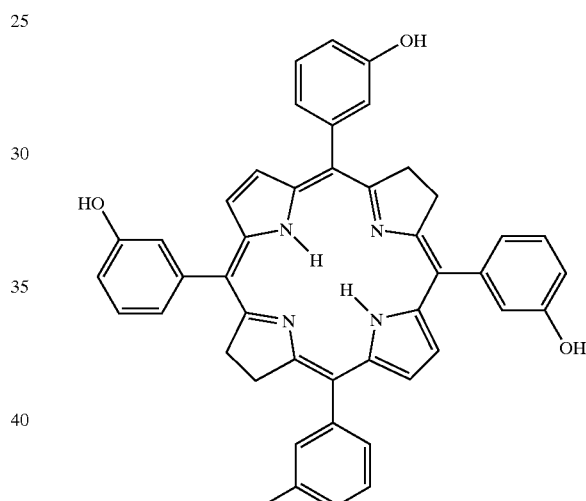
5,10,15,20-Tetrakis(m-hydroxyphenyl)chlorin:
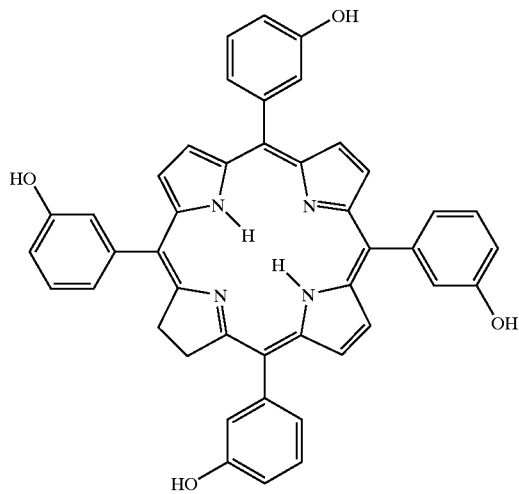
9-Acetoxy-2,7,12,17-tetrakis(ethoxyethyl)porphycene:
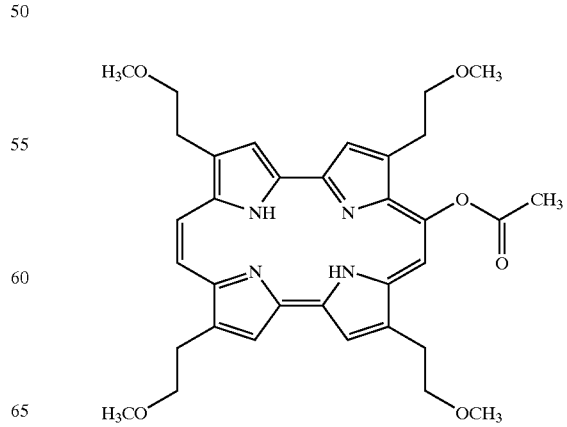

5,10,15,10-Tetrakis(m-hydroxyphenyl)porphyrine:

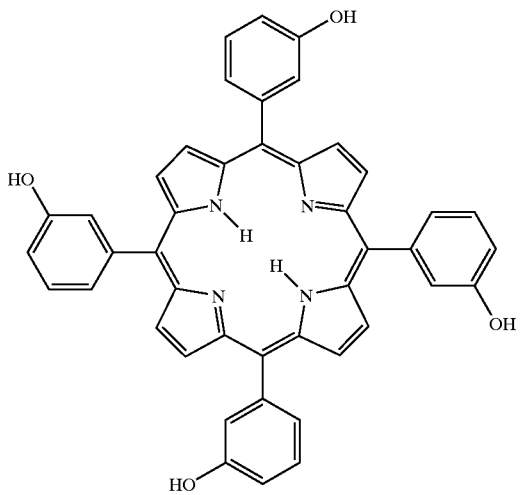

Coupling of the Photosensitizer to a Solid Carrier

The reaction sequence shown below shows the individual steps with which TCPcM can be coupled to a Sephadex or cellulose matrix.

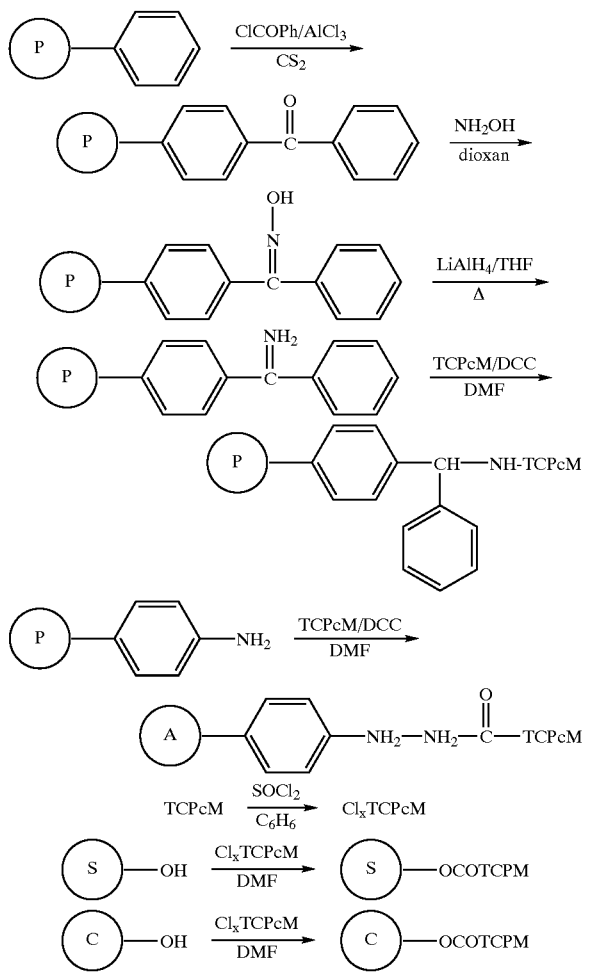

DCC = dicyclohexylcarbodiimide
DMF = dimethylformamide

In the above equation, the abbreviations used have the following meaning:
Ⓢ—OH: Sephadex
Ⓒ—OH: Cellulose

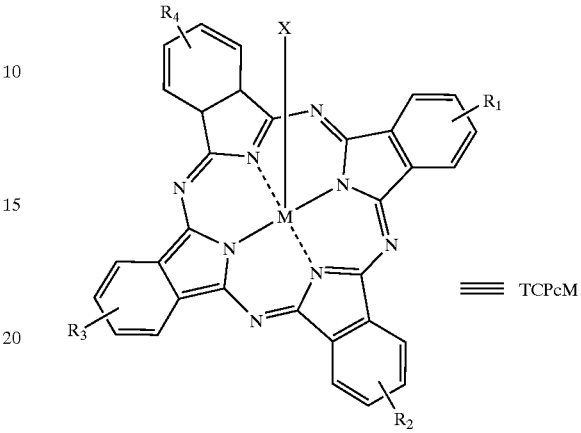

| TCPcM | $R_1$ | $R_2$ | $R_3$ | $R_4$ | X |
|---|---|---|---|---|---|
| TCPcCu | $CO_2H$ | $CO_2H$ | $CO_2H$ | $CO_2H$ | — |
| TCPcAl | $CO_2H$ | $CO_2H$ | $CO_2H$ | $CONH_2$ | CH |

Depending on the mode of binding, the photosensitization efficiency may be drastically enhanced or depressed.

Antimicrobial Activity of tetra(N-Methyl-pyridyl)-porphin ($T_4MPyP$) and cis-di-(N-Methyl-pyridyl)-diphenyl-porphin (di(4-N-MPy)$Ph_2P$)

In di(4-N-MPy)$Ph_2P$, the two N-methyl-pyridyl groups were attached to two adjacent rings, that is to say on the same side of the macrocyclic radical.

A particular feature of the dipyridyl derivative is that this molecule has a polarity sufficient for it to be water-soluble, while at the same time, on the other side of the macrocyclic radical, a hydrophobic matrix exists which facilitates interaction of the macrocyclic radical with non-polar domains of a cell (for example lipid regions of cellular membranes) and thus intensifies the binding and allows more efficient accumulation on the cell. Table 1 below shows that even after washing several times di(4-N-MPy)$Ph_2P$ is washed off neither from *E. seriolicida* (Gram-positive strain) nor from *V. anguillarum* or *E. coli* (Gram-negative strains). A greater reduction in the amount of cell-bound substance is. observed for $T_4MPyP$. It is concluded from this that compounds of the first type (di(4-N-MPy)$Ph_2P$) could display a better antibacterial action in aqueous systems than the compounds of the type $T_4MPyP$, although the latter also show antibacterial activity. Longer intimate contact between the photosensitizer and the bacterial cell increases the action of singlett oxygen, which is generated by the irradiation, on the bacterial cell.

Table 2 shows that di(4-N-MPy)$Ph_2P$ is taken up at the spheroplasts or protoplasts rather than at the outer cell wall. This means that the dicationic porphyrin appears to position itself in the endocellular compartments, which are particularly critical for the survival of the cell. The porphyrin concentration in these endocellular positions is again not noticeably decreased by washing operations; only the externally bound photosensitizer is removed.

On the other hand, $T_4MPyP$ is bound less efficiently to the spheroplasts or protoplasts and is removed more rapidly from the external and internal binding sites. From this, it can be concluded that di(4-N-MPy)Ph$_2$P seems to be a better photosensitizer for inactivation of bacteria compared with T$_4$MPyP.

Figure 1:
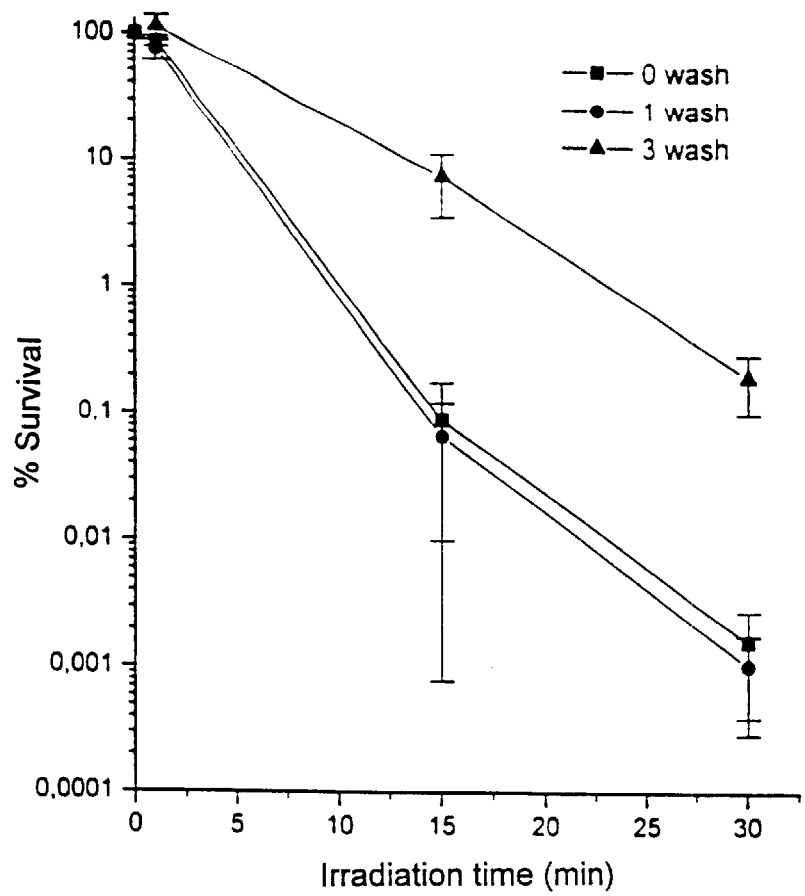
FIGS. 1–13 show the action of photosensitizers on various microorganisms as explained below.
Figure 2:
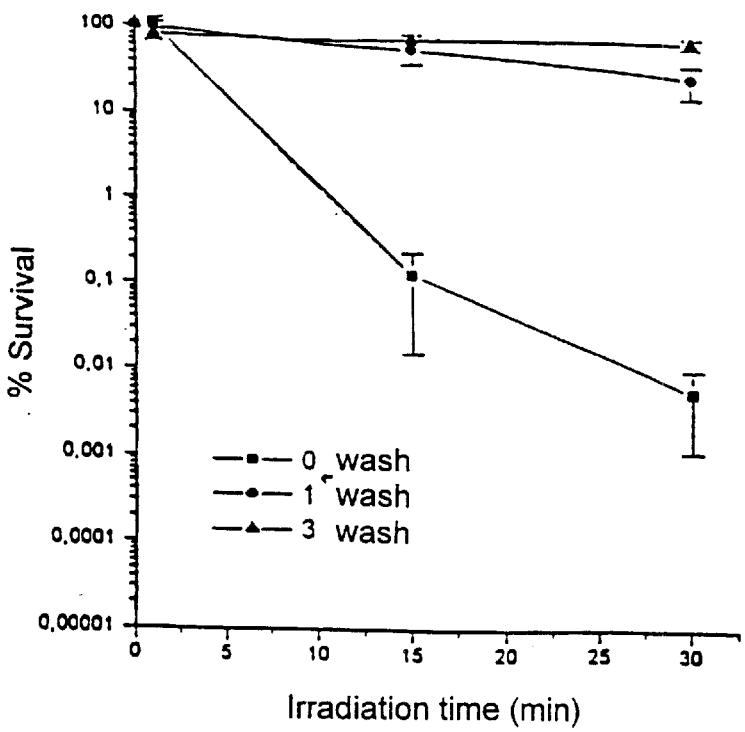
Figure 3:
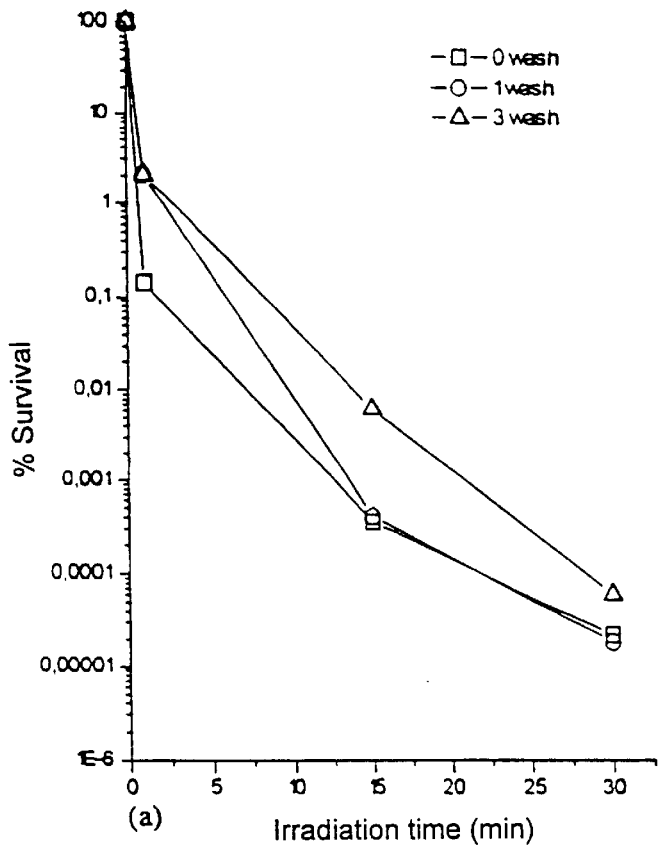
Figure 4:
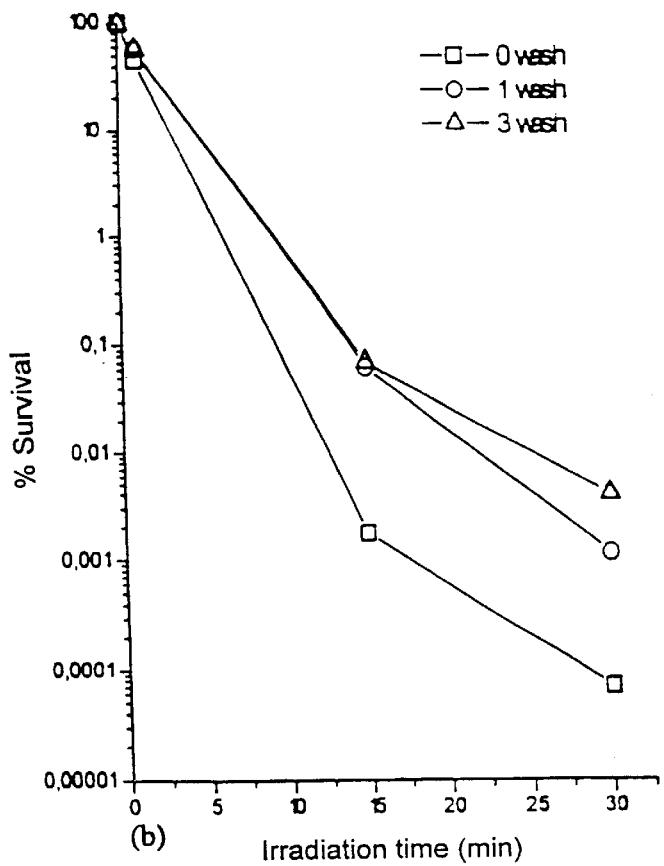
Figure 5:
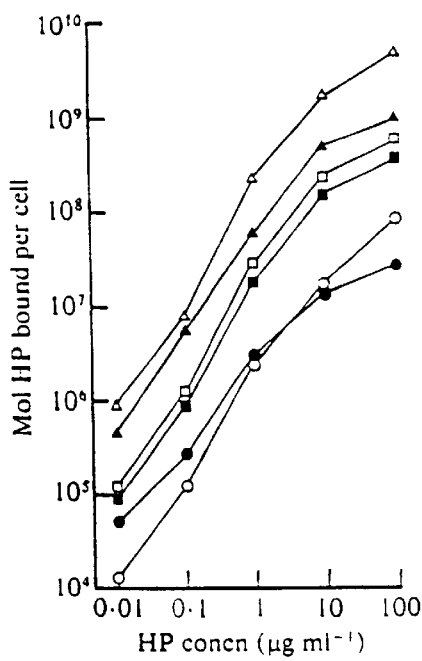
Figure 6:
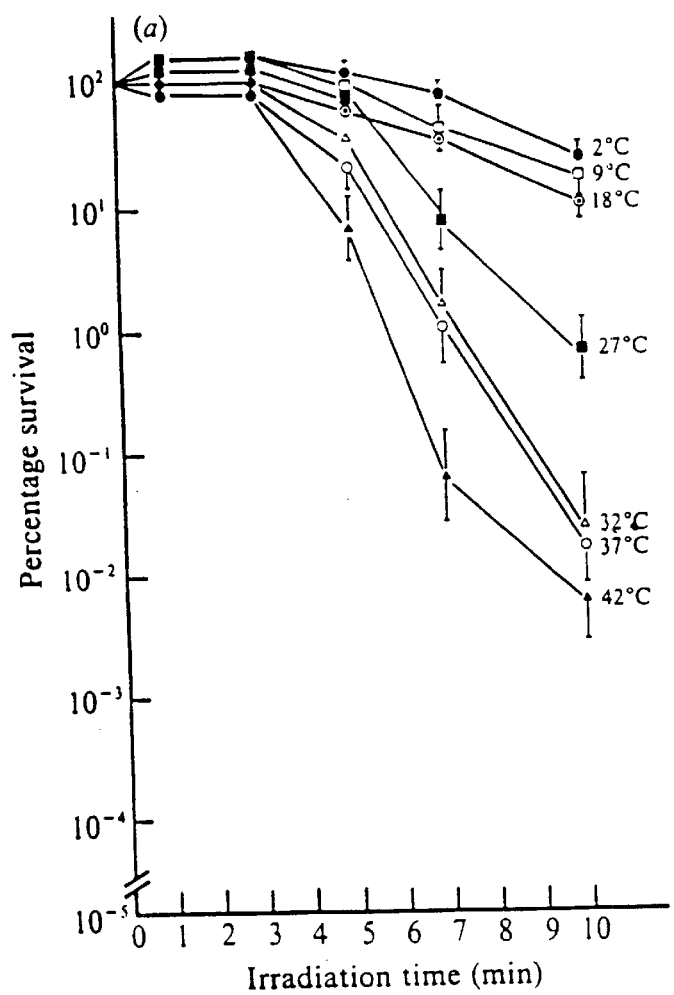
Figure 7:
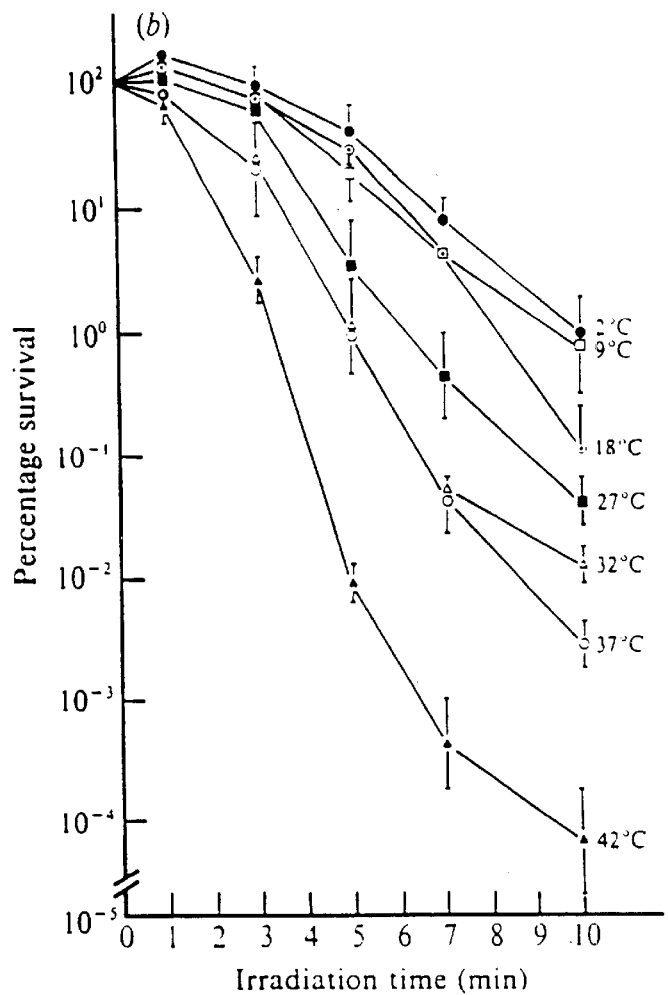
Figure 8:
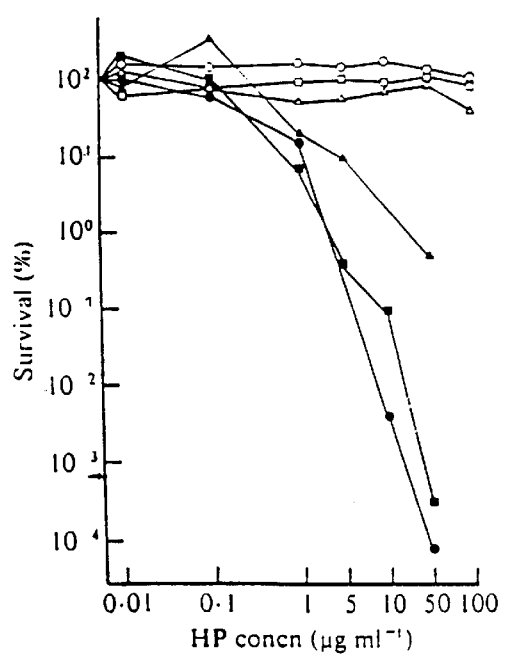
Figure 9:
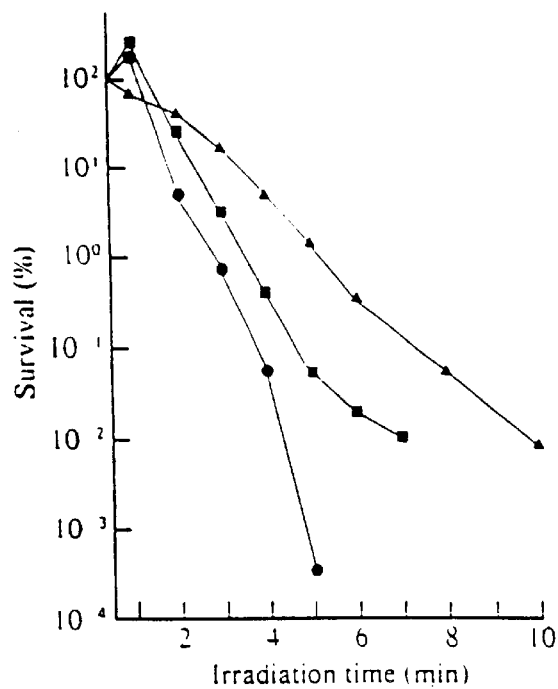
Figure 10:
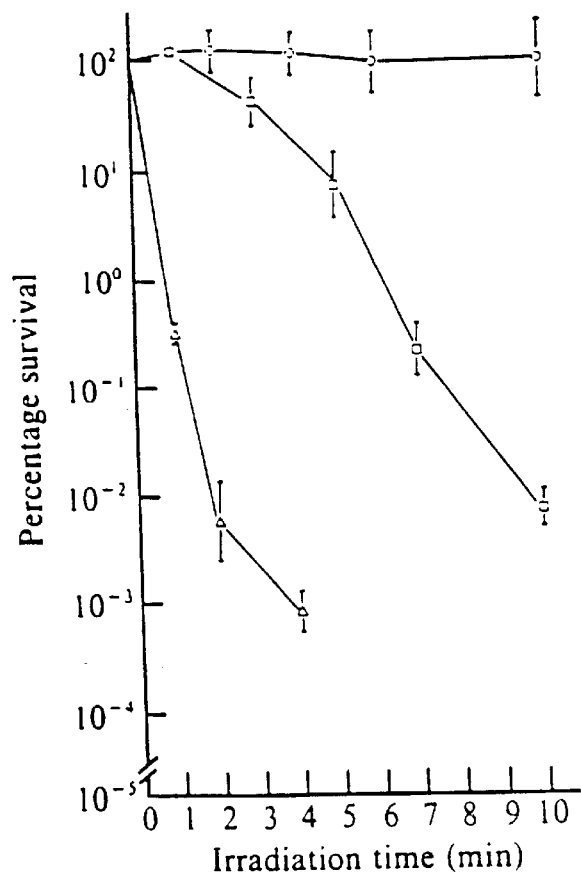
Figure 11:
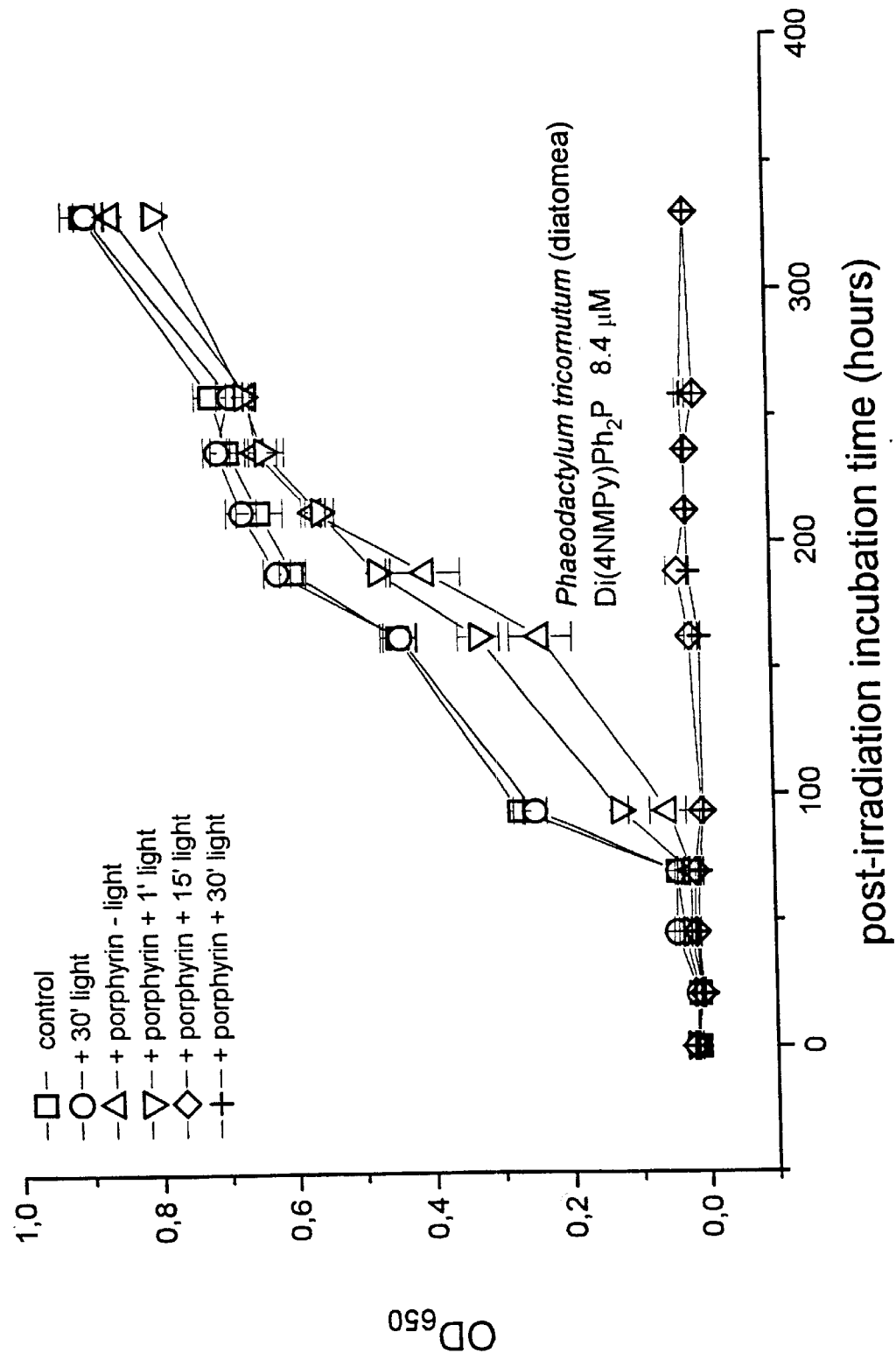
Figure 12:
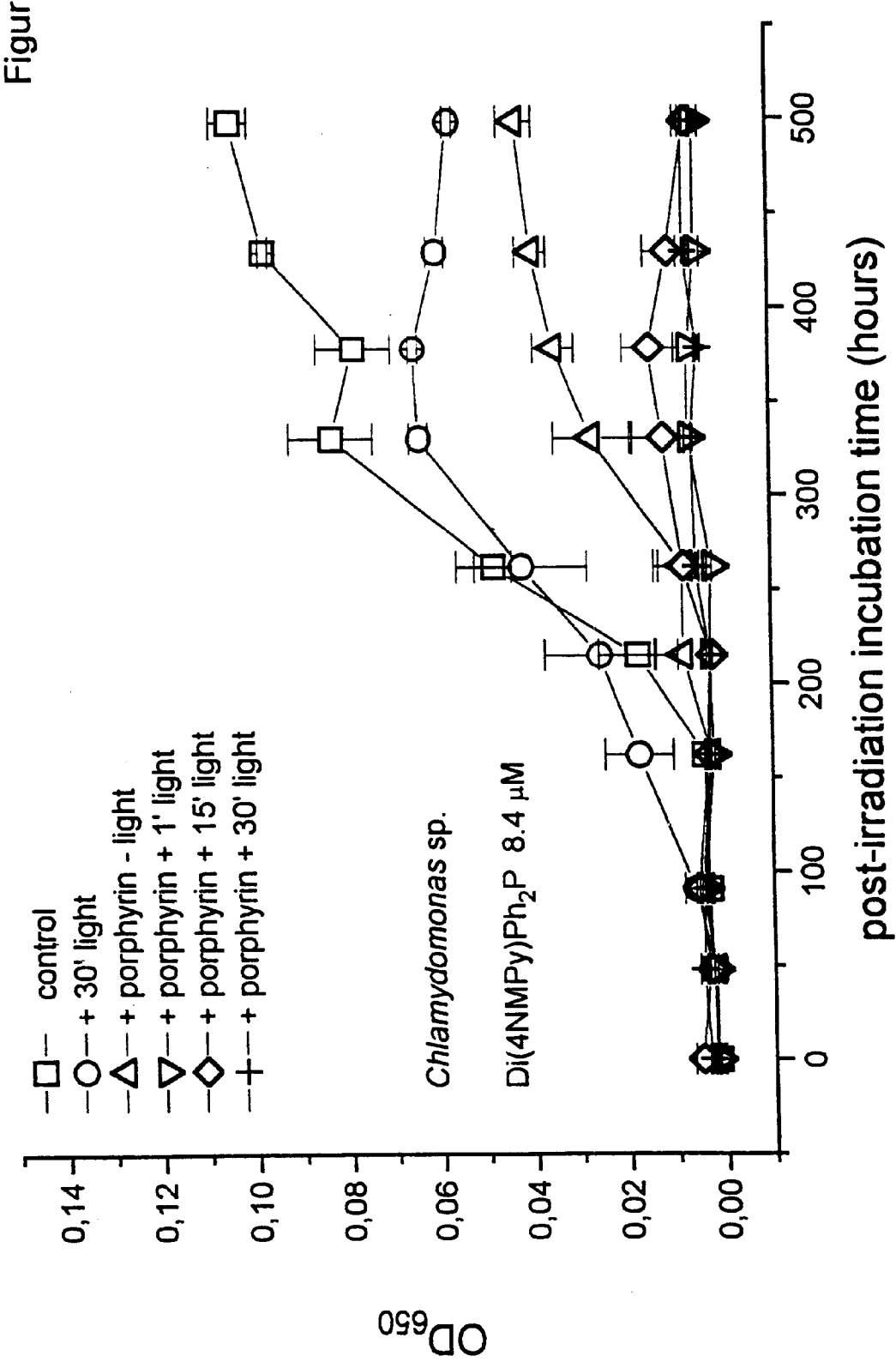

As can also be seen from FIG. 1, which shows the kinetics of the destruction of Gram-negative bacteria by photosensitizers, the efficiency of T$_4$MPyP decreases to a greater extent due to the washing operations. The dicationic porphyrin is less sensitive to washing and retains a high photoactivity. Furthermore, di(4-N-MPy)Ph$_2$P introduces a more rapid and more intense photo-inactivation of both *Vibrio anguillarum* and *Escherichia coli* than T$_4$MPyP.

TABLE 1

Recovery of meso-substituted porphyrins from selected Gram(+) and Gram(−) bacteria strains after 5 minutes of incubation with 8.4 μM photosensitizer and after various washing steps
Recovery (nMol/10$^6$ cells)

| Bacteria | washing operation | T$_4$MPyP | Di(4-N-MPy)Ph$_2$P |
|---|---|---|---|
| *E. seriolicida* | 0 | 7.80 ± 0.21 | 9.42 ± 0.41 |
| * | 1 | 1.00 ± 0.13 | 8.79 ± 0.03 |
|  | 3 | 0.63 ± 0.10 | 8.31 ± 0.10 |
| *V. anguillarum* | 0 | 8.0 ± 0.33 | 8.63 ± 0.25 |
| * | 1 | 1.20 ± 0.23 | 6.00 ± 0.50 |
|  | 3 | 0.59 ± 0.27 | 4.89 ± 0.10 |
| *E. coli* | 0 | 6.62 ± 0.25 | 8.75 ± 0.23 |
| ** | 1 | 1.35 ± 0.23 | 6.13 ± 0.10 |
|  | 3 | 1.17 ± 0.02 | 4.06 ± 0.02 |

*2% strength NaCl solution
**aqueous phosphate-buffered saline solution

TABLE 2

Recovery of meso-substituted porphyrins from the cell wall and protoplasts or spheroplasts of selected Gram(+) and Gram(−) bacteria strains after 5 minutes incubation with 8.4 μM photosensitizer and after various washing steps
Recovery (nMol/10$^8$ cells)

| Bacteria | washing operation | T$_4$MPyP | | Di(4-N-MPy)Ph$_2$P | |
|---|---|---|---|---|---|
| *E. seriolicida* | 1 | 0.24 ± 0.05 | 0.65 ± 0.05 | 0.11 ± 0.01 | 2.24 ± 0.04 |
| * | 3 | 0.01 ± 0.00 | 0.07 ± 0.01 | 0.01 ± 0.00 | 2.10 ± 0.02 |
| *V. anguillarum* | 1 | 0.23 ± 0.05 | 0.43 ± 0.05 | 0.20 ± 0.01 | 2.07 ± 0.02 |
| * | 3 | 0.01 ± 0.00 | 0.08 ± 0.01 | 0.12 ± 0.05 | 1.58 ± 0.03 |
| *E. coli* | 1 | 0.25 ± 0.01 | 0.61 ± 0.01 | 0.65 ± 0.01 | 2.08 ± 0.05 |
| ** | 3 | 0.01 ± 0.00 | 0.27 ± 0.02 | 0.45 ± 0.02 | 2.04 ± 0.05 |

W cell wall
S/P Spheroplasts or protoplasts
*2% strength aqueous NaCl solution
**phosphate-buffered saline solution Photophysical and Photochemical Characterization of Fixed Photosensitizers The photosensitizer activity of the derivative bound to a polymer can be determined by determination of the quantum yield and the life of the lowest excited triplet state and the quantum yield of the $^1O_2$ generation.

The first parameter can be determined, for example, by laser flash photolysis and diffuse reflectance. These measurements allow selection of a photosensitizer which has a sufficiently long half-life for the desired purpose to allow the reaction with oxygen in the ground state. The efficiency of the conversion of oxygen into $^1O_2$ is determined by determination of the emission of luminescence of $^1O_2$ in the near infrared region, a nitrogen-cooled Ge detector being used. Although this information is familiar to the expert for most photosensitizers, it may nevertheless be desirable to determine these data for a photosensitizer when it is bound to a particular inert carrier, in order thus to investigate, for example, steric hindrances or other modifications of the photophysical parameters. The reaction constant of the reaction of the photosensitizer with oxygen can furthermore be determined in comparison with the reaction constant with other substrates (for example unsaturated lipids, steroids or aromatic or sulphur-containing amino acids), in order to determine the selectivity of the $^1O_2$ generation. Those photosensitizers which generate exclusively $^1O_2$ are particularly preferred for use in the process according to the invention.

Process for Treatment of Water in a Fish Farming Unit

However, it is also possible for the process to be used in an advantageous manner in several areas of industry, if appropriate being adapted to the particular technical requirements.

In this application, the water is treated by transferrring the water from the fish pond into a container, the transparent walls of which are coated with the polymer-bonded photosensitizer. The container is irradiated with a number of light sources, the light sources allowing the light intensity to be controlled. After the water has been in contact with the photosensitizer with a predetermined contact time, it is fed again to the fish pond.

In this way, visible light/porphyrin treatment of water (both drinkable water or water to be used for irrigation purposes) can be used for decreasing the overall microbial population below any dangerous threshold, as well as for preventing any undue or excessive growth of algae, yeast and/or fungi.

Unit for the Treatment of Germ-containing Water

A flow-through reactor for sterilization of water essentially comprises the following elements:

i) a compound of the porphyrin type which has a multiple band absorption spectrum in the visible region, so that the compound can essentially be photoactivated by all wavelengths in the range from 350 to 900 nm.

ii) an inert carrier, such as a polymeric material of the Sephadex type or inorganic beads (for example clay), which are water-insoluble but preferably water-swellable and onto which the photosensitizer is attached covalently; as a consequence of the covalent bonding, the porphyrin will not dissolve, is not distributed in the aqueous medium and can be removed at any desired point in time.

iii) a device for excitation of the porphyrin compound by inexpensive reliable sources of visible light which are easy to handle and generate light which can penetrate deeply into the water; this allows uniform irradiation of large volumes.

iv) a volatile cytotoxic agent, in particular singlett oxygen ($^1O_2$), which is generated by the photosensitizor under irradiation; $^1O_2$ has a life of a few microseconds in water equilibrated with air, and can diffuse about 15 mm in distance before it is deactivated. The singlett oxygen generated then displays its inactivating action on the microorganisms.

A plant for the treatment of water is shown diagrammatically in FIG. 14. A cylinder 1, consisting of a plurality of layers, absorbs the bacteria from the water passed through it, while the rotation of the cylinder increases the efficiency of bacterial absorption. Disinfection is accomplished with the aid of the photosensitizers in the water, which is removed from the fish pond 2 without requiring any mechanical filtration beforehand. This water is passed to a photodecontamination unit 3 which contains the photosensitizer in polymer-bound form. The polymer is equilibrated with water, thereby extensively swelling in the water and permitting intimate contact between the photosensitizer and the pathogens. The tank is subsequently irradiated with lamps 5 which emit an appropriate spectrum and intensity (about 500 W). The sterilized water withdrawn from the decontamination unit is then passed with the aid of pumps 4 to the subsequent circuit. 5 represents a filtration unit. If required, this process can be repeated a number of times until an appropriate degree of sterilization of the water has been obtained.

The efficiency of decontamination can be monitored by, for example, determining the residual bacterial populations and the number of germs as a function of the various treatment processes. The rotating filters on which the microorganisms have been absorbed can also be investigated by electron microscopy or X-ray microanalysis in order to identify the. microorganisms absorbed thereon and to investigate their viability.

The composition according to the invention therefore enables the provision of water of improved quality and a reduction in the disease susceptibility of fish cultivated therein, and also renders unnecessary the use of chemical or biological waste products while sterilizing the water at the same time. If the photosensitizer should undergo photochemical degradation (at least in part) during the phototreatment, the possible formation of chemical products, potentially noxious, which enter the water system can be envisaged.

The composition according to the invention also has the advantage that, if applied in a process for water-treatment, only a small amount of waste is produced, the energy input is low, since inexpensive, visible light sources or sunlight are employed, and the process harbours little risk to the consumers of fish as a result of possible residues. Moreover, the selection of photoresistant microbial strains can be avoided, since the treatment is non-mutagenic.

I claim:

1. A composition comprising a solid carrier and more than one photosensitizer comprising a tetrapyrrole and/or tetraazapyrrole compound, wherein the carrier is swellable in water and is selected from the group consisting of polystyrol, sephadex and clay, and wherein the more than one photosensitizer are chemically bonded to the carrier, have different absorption maxima, and are selected such that the entire spectrum of visible light is utilized for photosensitization.

2. The composition according to claim 1, wherein the photosensitizer is selected from the group consisting of bacteriochlorins, chlorins, porphycenes, porphyrins, phthalocyanines, and naphthalocyanines.

3. The composition according to claim 1, wherein the photosensitizer contains at least one positive charge.

4. The composition according to claim 3, wherein the photosensitizer contains two positive charges located in the meso positions or in two adjacent pyrrole rings.

5. A process for combatting bacterial germs, algae, yeast and/or fungi in water comprising bringing the germ-, algae-, yeast-, and/or fungi-containing water into contact with a composition comprising a water-swellable solid carrier and at least one photosensitizer chemically bonded to the carrier, wherein the solid carrier is sephadex and the photosensitizer is Al-phthalocyanine tetracarboxylate, and subjecting the water to electromagnetic radiation while in contact with the composition.

6. The process according to claim 5, wherein the electromagnetic radiation is visible light of 350 nm to 900 nm.

* * * * *